United States Patent [19]

Ryf

[11] 4,080,392
[45] Mar. 21, 1978

[54] PROCESS FOR THE PRODUCTION OF AROMATIC TRIFLUOROMETHYL COMPOUNDS OF THE BENZENE SERIES

[75] Inventor: Kurt Ryf, Visp, Vs, Switzerland

[73] Assignee: Lonza Ltd., Gampel, Valais, Switzerland

[21] Appl. No.: 641,778

[22] Filed: Dec. 17, 1975

[30] Foreign Application Priority Data

Dec. 19, 1974 Switzerland ................. 16872/74

[51] Int. Cl.$^2$ ............................................. C07C 25/14
[52] U.S. Cl. .................................................. 260/651 F
[58] Field of Search ..................................... 260/651 F

[56] References Cited

U.S. PATENT DOCUMENTS

| | | | |
|---|---|---|---|
| 2,562,159 | 7/1951 | Wodcik et al. | 260/651 F |
| 2,654,789 | 10/1953 | Ligett | 260/651 F |
| 3,950,445 | 4/1976 | Ryf | 260/651 F |

OTHER PUBLICATIONS

McBee et al., (I), 69 JACS (1947), pp. 947–950.
McBee et al., (II), Prepn., Properties & Technology of Fluorine & Org. Fluoro Compds., (Slesser, Editor) 1st Ed., McGraw Hill, New York (1951).

*Primary Examiner*—C. Davis
*Attorney, Agent, or Firm*—Virgil H. Marsh

[57] ABSTRACT

An improved process for the production of aromatic trifluoromethyl compounds of the benzene series by conversion of the corresponding trichloromethyl compound with hydrogen fluoride. The aromatic trichloromethyl compound of the benzene series is converted in the presence of antimony pentachloride, which is a catalyst, in a quantity, related to the quantity of the trichloromethyl compound, of 200 to 700 ppm per trichloromethyl group in the trichloromethyl compound, with a stoichiometric quantity, or at most a 2 percent excess, of hydrogen fluoride. The conversion is conducted at a pressure of 20 to 45 atm., at a temperature of 60° to 75° C. and with intermixing which is characterized by a Reynolds number between 50,000 and 80,000. Yields of around 98 percent are achieved.

8 Claims, No Drawings

PROCESS FOR THE PRODUCTION OF AROMATIC TRIFLUOROMETHYL COMPOUNDS OF THE BENZENE SERIES

BACKGROUND OF THIS INVENTION

1. Field of This Invention

This invention relates to a process for the production of aromatic trifluoromethyl compounds of the benzene series by conversion of the corresponding trichloro methyl compounds using hydrogen fluoride.

2. Prior Art

It is known, that compounds having one or more trichloromethyl groups on one aromatic nucleus can be converted with hydrogen fluoride in the presence of antimony methyl compounds into the corresponding trifluoro methyl compounds (see Houbeu-Weyl, "Methods of Organic Chemistry", vol. 5/3, pp. 124 and 125).

In U.S. Pat. No. 2,654,789 a process is described for the production of p-bis-(trifluorometyl) benzene (see col. 4, line 55 etc.). The trichloro compound is converted with an excess of hydrogen fluoride in the presence of antimony pentachloride, which is present in a quantity of about 1.0 percent related to the trichloro compound, at a temperature of 100° C. and a pressure of about 34 atm. using a reaction time of around one hour into the corresponding trifluoro compound.

The known processes have the serious disadvantage of requiring large surpluses of hydrogen fluoride. For reasons of economy and of the protection of the environment, these surpluses must be recaptured, if possible, in order to feed them again into the reactor. Also, in order to carry out the reaction, relatively large quantities of antimony pentachloride are required as a catalyst. During the reaction the catalyst is decomposed, thereby becomes ineffective and must be continuously replaced.

BROAD DESCRIPTION OF THIS INVENTION

It is an object of this invention to provide a process which requires no, or only small quantities of, surplus hydrogen fluoride and in which no decomposition of the catalyst takes place. It is another object of this invention to provide a process which requires lesser amounts of catalysts. It is a further object of this invention to provide a process which lessens the corrosion of the reactors used and eliminate much of the potential pollution to the environment (along with the continual cost of prevention such potential pollution from becoming actual pollution). Other objects and advantages of this invention are set out herein or are obvious herefrom to one ordinarily skilled in the art.

The objects and advantages of this invention are achieved by this invention.

This invention involves a process for the production of aromatic trifluoromethyl compounds of the benzene series by conversion of the corresponding trichloromethyl compound with hydrogen fluoride. The aromatic trichloromethyl compound of the benzene series is converted in the presence of antimony pentachloride, which is a catalyst, in a quantity, related to the quantity of the trichloromethyl compound, of 200 to 700 ppm per trichloromethyl group in the trichloromethyl compound, with a stoichiometric quantity, or at most a 2 percent excess, of hydrogen fluoride. The conversion is conducted at a pressure of 20 to 45 atm., at a temperature of 60° to 75° C and with intermixing which is characterized by a Reynolds number between 50,000 and 80,000.

In case of the heretofore used reaction conditions, the reaction containers suffer considerable corrosion as a result of the presence of fairly large quantities of antimony compounds. Such corrosion no longer occurs in a practical sense under the conditions according to this invention.

DETAILED DESCRIPTION OF THIS INVENTION

Examples of aromatic trifluoromethyl compounds of the benzene series which can be produced according to the process of the invention from the corresponding trichloromethyl compounds are: benzotrifluoride, p-chlorobenzotrifluoride, 2,4-dichlorobenzotrifluoride, 1,4-bis-trifluoromethyl benzene, 1,2,4-tris-trifluoromethyl benzene, o-chlorobenzotrifluoride, m-chlorobenzotrifluoride, 1,3-bis-trifluoromethyl benzene, etc.

The catalyst used in this invention may be antimony pentachloride of commercial quality. The catalyst is used in quantities, related to the quantity of trichloromethyl compound used, of 200 to 700 ppm (preferably 250 to 600 ppm) per trichloromethyl group in the compound. Larger quantities of catalyst can be used, but no strong tendency for resinification occurs.

The conversion of the trichloromethyl compound with hydrogen fluoride and the distillation processing of the conversion mixture takes place according to known methods.

The conversion may be carried out in a pressure vessel, which is equipped with a stirrer.

The trichloromethyl compounds are reacted preferably, after their insertion into the reactor, in the presence of about 1 percent, related to the quantity of the starting trichloromethyl compound, of phosphorus trichloride. This addition of phosphorus trichloride serves to eliminate any possible small water content — such elimination of water having a favorable effect on the yield.

After the addition of the catalyst and hydrogen fluoride in stoichiometric quantities, the reaction components are brought to a temperature of 60° to 75° C. Preferably, a temperature of 68° to 72° C. is maintained during the reaction. At a reaction temperature over 100° C., the catalyst (used in this invention) quickly becomes inactive as a result of decomposition and at a reaction temperature below 60° C. the catalyst does not yet possess its full catalytic activity. The reaction pressure in the reactor is adjusted to between 20 and 45 atm. Preferably a reaction pressure of 35 to 40 atm. is maintained.

In order to carry out the reaction successfully, an excellent intermixing of the reaction components is necessary. The measure of such intermixing is characterized by the Reynolds number, which is defined as:

$$Re = (n \cdot d^2)/v$$

wherein $n$ = number of rotations of the stirrer (rotations/sec.), $d$ = diameter of the stirrer (m), and $v$ = kinematic viscosity ($m^2$/sec.). Useful (within the meaning of this invention) numerial values of the Reynolds number ranges from 50,000 to 80,000. Preferably the Reynolds number ranges from 58,000 to 62,000.

In the process of this invention which is sufficient to use hydrogen fluoride in a stoichiometric quantity or to use hydrogen fluoride in a surplus quantity of at most 1 to 2 percent. The 1 or 2 percent surplus of hydrogen fluoride is discharged according to their partial pressure along with the excess hydrochloric acid at reaction pressure. In the case of dosing, these losses must be taken into consideration in order to achieve a quantitative conversion. Yields of about 98 percent of the aromatic trifluoromethyl compounds of the benzene series are obtained by this invention.

The process of this invention can also be carried out continuously. In that case, the reaction is carried out up to a certain conversion under conditions according to this invention in a first reaction vessel; the reaction mixture is then placed in a second reaction vessel and the reaction is conducted under the same conditions until complete conversion of the reaction components is achieved.

The process according to this invention has the great advantage of a short reaction time. The optimum conversion and optimum yield are achieved already within 10 to 15 minutes. Preferably a reaction time of about 12 minutes is used.

The trifluoromethyl compound formed can be removed from the reaction vessel after completed reaction in the customary manner. The trifluoromethyl compound is purified by distillation, whereby the antimony pentachloride catalyst remains behind in the still — such antimony pentachloride catalyst can be recovered quantitatively and used again.

As used herein, all parts, ratios, percentages and proportions are on a weight basis, unless otherwise stated or otherwise obvious herefrom to one ordinarily skilled in the art.

EXAMPLE 1

391 gm. (2 moles) of freshly distilled benzotrichloride (also termed α-trichlorotoluene) was placed in a pressure resistant, one liter, steel autoclave with brine cooled reflux cooler and was heated to 70° C. Then 122 gm. (6.1 moles) of anhydrous hydrogen fluoride was added in the autoclave from a cooled measuring tube. The pressure in the autoclave was raised to 40 atm. with nitrogen. The temperature of the reaction mixture was kept automatically at 70° C. by controlled heating of the autoclave. The hydrochloric acid which developed during the reaction, after passing the cooler, was discharged continuously into a masher by means of a pressure regulating valve. After 12 minutes of reaction a sample of the organic product was taken, washed with water and dried. Gas chromatographic analysis of the organic product showed a content of 71 mole percent benzotrifluoride, 28.6 mole percent α, α-difluoro-α-chlorotoluene and 0.3 mole percent α,α-dichloro-α-fluorotoluene.

EXAMPLE 2

In this experiment Example 1 was repeated except that 250 ppm of antimony pentachloride (based on the amount of benzotrichloride used) were added to the reactants in the autoclave at the start of the experiment. The discharged product was filtered, washed and dried. The gas chromatographic analysis of the organic product showed a content of 98 mole percent benzotrifluoride and 1.9 mole percent α-α-difluoro-α-chlorotoluene.

EXAMPLE 3

In order to determine the effect of intermixing on the reaction speed, the reaction was carried out in a series of experiments using various stirring speeds. At each stirring speed, the conditions, amounts, etc., of Example 1 were used and then repeated using 250 ppm of $SbCl_5$ (as in Example 2). The reaction samples were taken after a reaction time of 12 minutes and processed according to the customary method and analysed (as in Example 1). The yields of benzotrifluoride are seen in Table 1.

TABLE 1

| | | Reynolds Number | | | | |
|---|---|---|---|---|---|---|
| | | 20,000 | 40,000 | 60,000 | 80,000 | 100,000 |
| Yield* mole percent | with $SbCl_5$ (250 ppm) | 81 | 93 | 98 | 98 | 98 |
| | without $SbCl_5$ | — | 47 | 63 | 69 | 71 |

*of benzotrifluoride

EXAMPLE 4

In this series of experiments, with otherwise the same method of operation as in Example 2, at constant flow conditions, which was characterized by Reynolds number of $Re = 60,000$, the reaction temperature was varied. The results are summarized in Table 2:

TABLE 2

| Temperature, °C | 60 | 65 | 68 | 70 | 72 | 75 | 80 |
|---|---|---|---|---|---|---|---|
| Yield of benzotrifluoride, mole percent | 92 | 95 | 97 | 98 | 98 | 96 | 93 |

EXAMPLE 5

Under the conditions described in Example 2, 460 gm. (2 moles) of p-chlorobenzotrichloride was reacted with 122 gm. (6.1 moles) of anhydrous hydrogen fluoride. The sample taken after a reaction time of 12 minutes was processed according to the method of Example 1 and analyzed. The yield of p-chlorobenzotrifluoride amounted to 97 mole percent.

EXAMPLE 6

460 gm. (2 moles) of o-chlorobenzonitrifluoride was mixed with 500 ppm of antimony pentachloride and was converted with 122 gm. (6.1 moles) of anhydrous hydrogen fluoride at a temperature of 70° C. and a pressure of 40 atm. The gas chromatographic analysis of the reaction product, after a reaction time of 12 minutes showed a content of 97 mole percent o-chlorobenzotrifluoride.

EXAMPLE 7

522 gm. (2 moles) of 2,4-dichloro-benzotrichloride was reacted under the reaction conditions described in Example 6. The analysis of the reaction sample after 12 minutes showed a content of 97.5 mole percent 2,4-dichloro-benzotrifluoride.

What is claimed is:

1. The process for the production of aromatic trifluoromethyl compounds of the benzene series by conversion of the corresponding trichloromethyl compound with hydrogen fluoride, characterized in that said aromatic trichloromethyl compound of the benzene series is reacted in the presence of antimony pentachloride catalyst in an amount, related to the amount of said trichloromethyl compound, of 200 to 700 ppm per trichloromethyl group in said trichloromethyl compound, with a stoichiometric amount, or at most a 2 percent excess, of hydrogen fluoride at a pressure of 20 to 45 atm., at a temperature of 60° to 75° C., with intermixing which is characterized by a Reynolds number between 50,000 and 80,000, and for a time period of 10 to 15 minutes.

2. The process of claim 1 wherein said antimony pentachloride is used in a quantity, related to the quantity of said trichloromethyl compound, of 250 to 600 ppm per trichloromethyl group in said trichloromethyl compound.

3. The process of claim 1, wherein said conversion is conducted at a pressure of 35 to 40 atm.

4. The process of claim 1 wherein said conversion is conducted at an intermixing which is characterized by a Reynolds number between 58,000 to 62,000.

5. The process of claim 1 wherein said reaction or conversion is carried out in the presence of sufficient phosphorous trichloride to dry said reaction mixture.

6. The process of claim 1 wherein said process is carried out on a continuous basis.

7. The process of claim 1 wherein said trichloromethyl compound is purified by distillation.

8. The process of claim 1 wherein said antimony pentachloride is used in a quantity, related to the quantity of said trichloromethyl compound, of 250 to 600 ppm per trichlorometyl group in said trichloromethyl compound, said conversion is conducted at an intermixing which is characterized by a Reynolds number between 58,000 and 62,000, said reaction or conversion is carried out in the presence of sufficient phosphorous trichloride to dry said reaction mixture, said resultant trifluoromethyl compound is purified by distillation.

* * * * *